United States Patent
Pappas

(10) Patent No.: US 10,413,563 B2
(45) Date of Patent: Sep. 17, 2019

(54) NEUROCHEMICAL WELLNESS PROGRAM

(71) Applicant: Emerald Neuro-Recover, LLC, Cicero, IN (US)

(72) Inventor: Joseph W. Pappas, Westfield, IN (US)

(73) Assignee: Emerald Neuro-Recover, LLC, Carmel, IN (US)

( * ) Notice: Subject to any disclaimer, the term of this patent is extended or adjusted under 35 U.S.C. 154(b) by 0 days.

(21) Appl. No.: 15/974,909

(22) Filed: May 9, 2018

(65) Prior Publication Data

US 2018/0325935 A1 Nov. 15, 2018

Related U.S. Application Data

(60) Provisional application No. 62/504,097, filed on May 10, 2017.

(51) Int. Cl.

| A61K 31/7084 | (2006.01) |
| A61K 31/198 | (2006.01) |
| A61K 45/06 | (2006.01) |
| A61K 9/00 | (2006.01) |
| A61K 31/451 | (2006.01) |
| A61K 33/00 | (2006.01) |
| A61N 5/06 | (2006.01) |

(52) U.S. Cl.
CPC ........ *A61K 31/7084* (2013.01); *A61K 9/0019* (2013.01); *A61K 31/198* (2013.01); *A61K 31/451* (2013.01); *A61K 33/00* (2013.01); *A61K 45/06* (2013.01); *A61N 2005/0661* (2013.01)

(58) Field of Classification Search
CPC .............. A61K 9/0019; A61K 31/7084; A61K 31/198; A61K 33/00; A61N 2005/0661
See application file for complete search history.

(56) References Cited

U.S. PATENT DOCUMENTS

| 5,308,627 | A | 5/1994 | Umbdenstock |
| 5,332,579 | A | 7/1994 | Umbdenstock |
| 5,559,152 | A | 9/1996 | Komissarova et al. |
| 5,888,532 | A | 3/1999 | Pritsos et al. |
| 7,993,381 | B2 | 8/2011 | Mac et al. |
| 8,003,324 | B2 | 8/2011 | Dudley |
| 9,669,199 | B2 | 6/2017 | DiPierro et al. |
| 2003/0021772 | A1* | 1/2003 | Birkmayer ........... A61K 31/711 424/94.1 |
| 2004/0248819 | A1* | 12/2004 | McGregor ......... A61K 31/7004 514/23 |
| 2009/0156649 | A1 | 6/2009 | Bunqer |
| 2010/0234308 | A1* | 9/2010 | Komatsu .................. A23L 2/52 514/17.7 |
| 2011/0288044 | A1 | 11/2011 | Dudley |
| 2017/0182299 | A1 | 6/2017 | DiPierro et al. |
| 2017/0224911 | A1 | 8/2017 | DiPierro et al. |

FOREIGN PATENT DOCUMENTS

WO   WO-2010041647 A1 *   4/2010   ............... A23L 2/52

OTHER PUBLICATIONS

Arita et al., machine translation of WO 2010/041647 A1 (retrieved from translate.google.com Aug. 2018). (Year: 2018).*
Kim et al., Acupuncture for chronic fatigue syndrome and idiopathic chronic fatigue: a multicenter, nonblinded, randomized controlled trial, Trials (2015) 16:314. (Year: 2015).*

* cited by examiner

*Primary Examiner* — Theodore R. West
(74) *Attorney, Agent, or Firm* — Daniel L. Boots; Brian W. Chellgren; Bingham Greenebaum Doll LLP

(57) ABSTRACT

A novel process for improving neurochemical health includes a multi-day treatment program including intravenous delivery of nicotinamide adenine dinucleotide (NAD) to at least partially restore a patient's brain to a desired chemical balance. Intravenous delivery of NAD is synergistically combined with delivery of selected amino acids and, depending on the ailment being treated, a combination of ozone, testosterone, glutathione, Myers cocktail or other specified compounds.

21 Claims, 4 Drawing Sheets

NEUROCHEMICAL WELLNESS PROGRAM

This application claims the benefit of U.S. provisional patent application Ser. No. 62/504,097, filed May 10, 2017, for ADDICTION RECOVERY PROCESS, incorporated herein by reference.

FIELD OF THE INVENTION

A novel process for improving neurochemical health includes a multi-day treatment program including intravenous delivery of nicotinamide adenine dinucleotide (NAD) to at least partially restore a patient's brain to a desired chemical balance. Intravenous delivery of NAD is synergistically combined with delivery of selected amino acids and, depending on the ailment being treated, a combination of ozone, testosterone, glutathione, Myers cocktail or other specified compounds.

BACKGROUND OF THE INVENTION

The present invention relates to a process for improving neurochemical health. This process is useful for addiction recovery, such as drug addiction recovery, alcohol addiction recovery, or tobacco addiction recovery, as well as treating chronic fatigue, anxiety, and depression, and generally improving a patient's feeling of well-being. Alcohol and mood altering drugs (prescription or illegal) work by either mimicking the action of neurotransmitters, or artificially stimulating or suppressing them. Different drugs affect different neurotransmitters and their receptors. Continued substance abuse decreases the natural ability of neurons to send or receive signals. The human brain is not designed for prolonged or heavy exposure to chemicals that are not native to the body. An addicted user's body often does not have adequate quantities of natural energy for protein repair to restore the user's brain to a pre-addiction chemical balance. Abrupt withdrawal can be a shock to the user's system, while gradually cutting down can be a very slow and painful process, often resulting in failure. Oftentimes, withdrawal also results in anxiety, depression, insomnia, and other unpleasant symptoms. Consequently, a user's nervous system becomes physically and chemically dependent upon the substances and the continued use thereof to maintain feelings of normality and avoid withdrawal symptoms.

Current processes for addiction recovery typically do not address the underlying neurochemical changes in the brain caused by prolonged drug, alcohol or tobacco use. Abstinence, psychological support, and substituting other drugs are commonly all that are used in drug treatment programs. Other recovery processes are designed as if the brain will gradually recover naturally (that is, on its own) from the chemical damage. Although some degree of natural healing will typically occur after discontinuing drug or alcohol use, the extent of such healing is minimal, and the person suffers with the continuing physical and emotional discomforts of feelings of emptiness, anxiety, depression, insomnia, cravings, pain, difficulty maintaining concentration, fatigue and other undesirable symptoms. A need exists for novel systems for addiction recovery that address the medical condition of the brain and neurotransmitters to assist a user to at least partially achieve a pre-addiction chemical balance.

SUMMARY

Intravenous ("IV") β-nicotinamide adenine dinucleotide ("NAD", collectively referring to the compound in both its oxidized form "NAD+" and its reduced form "NADH") therapy directly addresses chemical damage caused to a user's brain by drugs, alcohol or tobacco. Neurons send signals to one another using a variety of chemicals neurotransmitters, such as serotonin, dopamine, and norepinephrine, A neurotransmitter is emitted by one neuron and is picked up by specialized receptors on neighboring neurons. These normal nerve pathways cease to function properly in an addict's brain. The present disclosure includes use of novel compositions for recovery of normal neurological chemical balance, the compositions including amino acids and other naturally occurring compounds, such as enzyme cofactors including NAD.

Application of NAD and specific combinations of amino acids, namely, L-threonine, glycine, L-phenylalanine, DL-phenylalanine (a mixture, preferably racemic, of D-phenylalanine and L-phenylalanine), and alanylglutamine dipeptide (a dipeptide comprising a L-alanine residue and a L-glutamine residue), via IV delivery has been observed to assist the brain's natural healing processes. This results in rapid restoration of brain functions with minimum withdrawal symptoms, even when abruptly discontinuing drugs or alcohol usage. The disclosed herein has been found to quickly improve symptoms of drug and alcohol dependence over a 10-day period, to an extent that would otherwise take several years to occur naturally.

Neuro recover treatment preferably involves several consecutive days of intravenous (IV) treatment. The IV formula is given as a slow drip requiring 6 to 10 hours each day. The prolonged daily exposure to high levels of amino acids effectively penetrate the brain, allowing the patient who may still use drugs or alcohol to safely stop using these substances completely, often on the first day of treatment. While some withdrawal symptoms will likely be felt, most patients find that it is much less severe than treatment without the assistance of the benefits of this novel process. Patients commonly find that the major negative effects of drug or alcohol use, such as cravings and anxiety, are typically gone by the fourth to sixth day of treatment. The treatment further improves, among other things, the patient's enthusiasm, memory, mental clarity, sleep quality and energy. A trained physician will determine how many days of customized treatment are required for optimal and lasting results for each individual patient.

Patients can expect the positive effects of neuro-recovery treatment to be long lasting, provided the patient refrains from using damaging and harmful substances again. Patients will typically be supplied with oral supplements to be taken during and after the IV therapy is completed. Continued use of the supplements according to treatment process guidelines supports the ongoing maintenance of the brain's proper chemical balance. Repeat IV treatments are seldom needed, although some patients benefit from a periodic booster now and then.

The treatment disclosed herein optionally further includes ozone therapy. Ozone ($O_3$) is an energized form of oxygen that contains three atoms of oxygen rather than the two atoms ($O_2$) we normally breathe. Ozone treats the root cause of many illnesses by targeting and destroying infectious organisms, such as parasites, yeast, fungus, mold, bacteria, and viruses. Providing a patient with controlled amounts of ozone balances the immune system, stimulates oxygen uptake and utilization in the body, and improves circulation. Ozone also has anti-inflammatory and anti-microbial properties. Ozone therapy has been used to treat allergies, sinusitis, arthritis, degenerative joint disease, auto-immune disease, back pain, cancer, chronic infections (such as Lyme disease), hepatitis, chronic pain, dental infections, ear infections, eye disease, fibromyalgia, intestinal diseases, skin disease, and promotes wound healing.

The treatment disclosed herein optionally includes testosterone replacement therapy. Prolonged use of opioids and certain other addictive compounds have been shown to result in low testosterone levels in both men and women. Providing testosterone replacement therapy facilitates the patient's return to a healthy chemical balance and feelings of vitality and wellbeing.

Embodiments disclosed herein provide a method for neurochemical wellness comprising delivering a first liquid composition to a patient intravenously, the first liquid composition including NAD, threonine, glycine, phenylalanine, and alanylglutamine dipeptide. In some embodiments, the method includes delivering the first liquid composition at least once per day for at least two days, at least once per day for at least nine days or at least once per day for nine to nineteen days. In further embodiments, the method includes delivering the first liquid composition once per day for at least nine days or at least once per day for nine to nineteen days. In certain embodiments, the first liquid composition is delivered to the patient intravenously between 8 hours and 12 hours per day for at least two days. In some embodiments, the first liquid composition includes at least about 900 mg NAD. In further embodiments, the first liquid composition includes between about 900 mg and 1200 mg NAD. In certain embodiments, the first liquid composition includes a mixture of D-phenylalanine and L-phenylalanine. In some embodiments, the first liquid composition includes a first quantity of L-threonine, glycine, and L-phenylalanine, and a second quantity of DL-phenylalanine and alanylglutamine dipeptide, and wherein the second quantity is greater than the first quantity or the second quantity. In further embodiments, the method further includes delivering a second liquid composition to the patient intravenously, the second liquid composition including a plurality of vitamins and a plurality of minerals. In certain embodiments, the second liquid composition includes B-vitamins, vitamin C, magnesium, and calcium. In some embodiments, the second liquid composition further includes one of glutathione and alpha lipoic acid. In further embodiments, the second liquid composition includes only one of glutathione and alpha lipoic acid. In certain embodiments, the second liquid composition is delivered to the patient on a plurality of days, the plurality of days being divided into non-overlapping first portion and second portion, and wherein the second liquid composition includes alpha lipoic acid during the first portion and wherein the second liquid composition includes glutathione on the second portion. The some embodiments, the first portion is three to nine days. In further embodiments, the second liquid composition includes between 500 mg and 1,000 mg glutathione. In certain embodiments, the second liquid composition includes about 25 mg alpha lipoic acid. In further embodiments, the method includes delivering the second liquid composition at least once per day for at least two days, at least once per day for at least nine days or at least once per day for nine to nineteen days. In further embodiments, the method includes delivering the second liquid composition once per day for at least nine days or at least once per day for nine to nineteen days. In certain embodiments, the second liquid composition is delivered to the patient intravenously between 30 minutes and one hour per day for at least two days. In some embodiments, the method further comprises delivering ozone to the patient intravenously. In further embodiments, the method further comprises drawing blood from the patient, infusing the blood with ozone, and intravenously delivering the blood back to the patient. In certain embodiments, the method further comprises drawing blood from the patient, exposing the blood to UV light, and intravenously delivering the blood back to the patient. In some embodiments, the method further comprises providing to the patient at least one of acupuncture treatment, chiropractic adjustment, testosterone replacement therapy, massages, application of pain cream, ozone therapy, UV light therapy, and oral supplements of niacin and NAD.

Embodiments disclosed herein provide a method for neurochemical wellness comprising delivering a first liquid composition to a patient intravenously, the first liquid composition including nicotinamide adenine dinucleotide, threonine, glycine, phenylalanine, and alanylglutamine dipeptide; and delivering a second liquid composition to the patient intravenously, the second liquid composition including a plurality of vitamins, a plurality of minerals, and glutathione; wherein the first liquid composition and the second liquid composition are each delivered to the patient at least once per day for a plurality of days.

Embodiments disclosed herein provide an addiction recovery process comprising delivering a first liquid composition to a patient intravenously, the first liquid composition including nicotinamide adenine dinucleotide, threonine, glycine, phenylalanine, and alanylglutamine dipeptide; and delivering a second liquid composition to the patient intravenously, the second liquid composition including a plurality of vitamins, a plurality of minerals, and glutathione; wherein the first liquid composition and the second liquid composition are each delivered to the patient at least once per day for a plurality of days.

This summary is provided to introduce a selection of the concepts that are described in further detail in the detailed description and drawings contained herein. This summary is not intended to identify any primary or essential features of the claimed subject matter. Some or all of the described features may be present in any corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present invention will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1A:
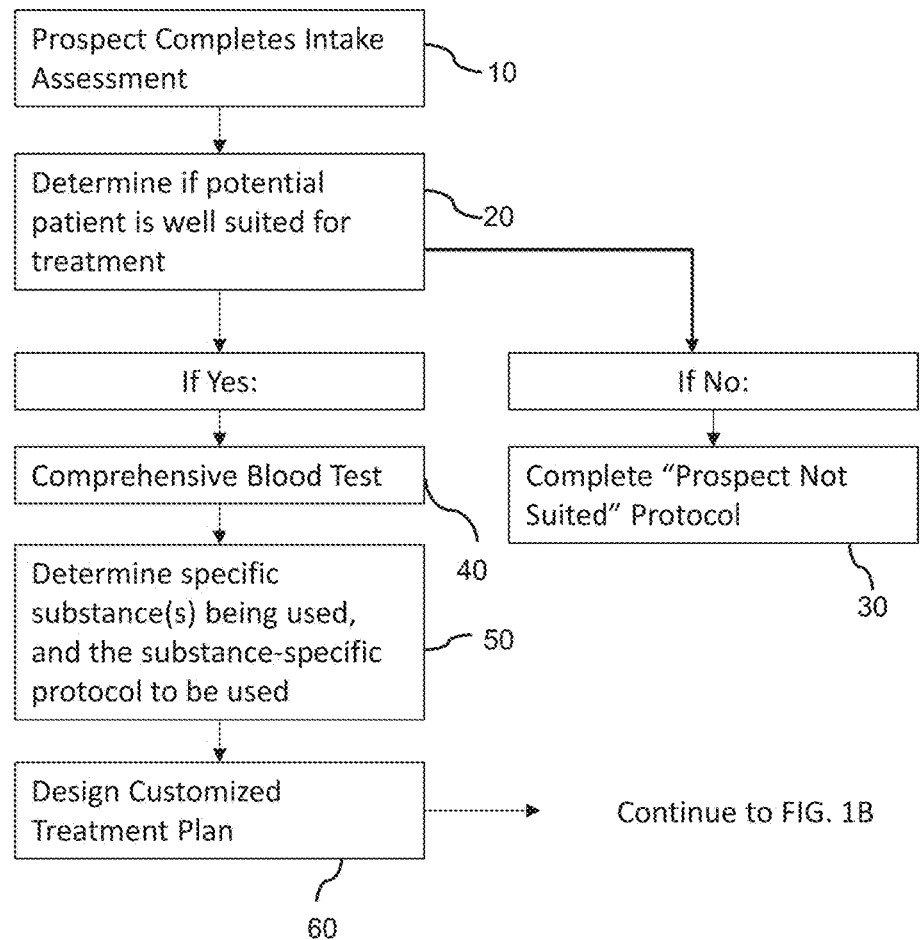
FIGS. 1A and 1B depict a flowchart presenting an embodiment of the novel process provided by this invention.

For the purposes of promoting an understanding of the principles of the invention, reference will now be made to selected embodiments illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any claim(s).

Any reference to "addictive substance" within this document is a reference to both tangible addictive substances (e.g., drugs and alcohol) and intangible addictive substances (e.g., gambling, pornography, sex), and is intended to be interpreted broadly unless expressly used otherwise.

While the present invention is primarily discussed in terms of neuro-wellness and/or of an addiction recovery process, it should be understood that this example is not intended to be limiting, and that the present invention may also be used to treat chronic fatigue, anxiety, depression, and other disorders, and to generally improve a patient's feeling of well-being.

Any specific quantities (spatial dimensions, dimensionless parameters, etc.) used explicitly or implicitly herein are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated. Specific quantities described with the phrase "about" or similar language (e.g., about 100 grams) are intended to convey a range of quantities ±5% of the stated value unless otherwise specified (e.g., "about 100 grams" indicates a range from 95 grams to 105 grams).

Figure 1B:
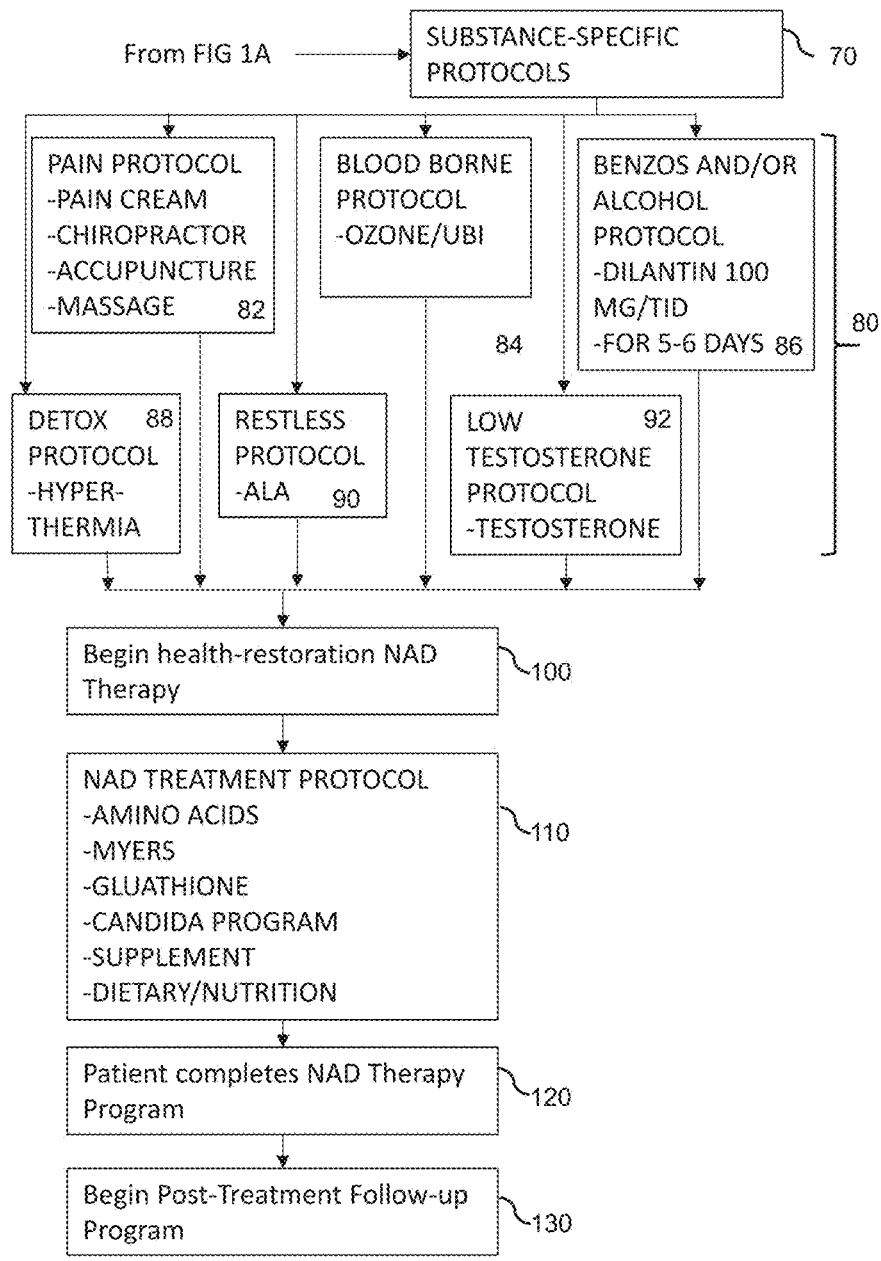

In one embodiment, as shown in FIGS. 1A-1B, a novel neurochemical wellness program includes the following series of steps taken preferably over sequential days:

Day 1

Initially, the patient preferably undergoes a medical psychiatric evaluation/consultation, which typically takes approximately 60 minutes, as shown in Box 10. The evaluator uses the results of the evaluation/consultation to determine if the potential patient satisfies addiction treatment criteria (Box 20). The potential patient is considered to satisfy addiction treatment criteria if: (1) the potential patient expresses the desire to discontinue use of the addictive substance to be treated; and (2) the potential patient expresses willingness to change elements in his or her environment that are conducive to addictive behavior. If the potential patient does not satisfy the addiction treatment criteria, he or she does not continue the treatment process (Box 30).

For patients who satisfy the addiction treatment criteria, the process continues with a comprehensive blood testing including of CBC (complete blood count), CMP (comprehensive metabolic panel), G6PD (screen for glucose-6-phosphate dehydrogenase deficiency), CRP (screen for C-reactive protein, a blood test marker for inflammation), Sed, Rate (erythrocyte sedimentation rate, a blood test to screen for inflammation), collection of urine (repeated daily for detection and monitoring of drugs or alcohol present in the patient's body), testosterone levels, and a pregnancy test (female patients only) (Box 40). If the daily collection of urine reveals an increase in drugs in the patient's body, treatment of the patient may be terminated at the physician's discretion.

A customized treatment plan is then designed for each patient depending on the substance abused by the patient, the quantity of substance in the patient's body, the duration of the patient's substance abuse, the patient's physical health, and any other factor considered relevant by the treating physician (Boxes 50, 60, 70 and 80). A standard treatment protocol is described below. The standard protocol as described in Day 2 and following Days may be customized with additional treatments based on the individual patient's condition.

In the event the patient suffers from pain (Box 82), the standard protocol is modified to include chiropractic assessment and adjustment and acupuncture assessment and treatment, massages and application of pain cream.

In the event the patient suffers from a blood borne viral pathogen (Box 84), such as, for example, hepatitis C or HIV, the standard protocol is modified to include intravenous ozone with ultraviolet blood irradiation, which comprises extracting a volume of blood from a patient, subjecting the blood to UV light, infusing ozone into the extracted blood, and returning the blood to the patient. In certain embodiments, ozone is administered by Major Auto Hemo Therapy, which includes the removal of 60 cc blood from the patient and injecting the blood into an IV saline solution. The blood is then ozonated by injecting a syringe containing a 60 cc mixture of ozone and medical grade oxygen (40%-70% ozone, 30%-60% oxygen) into the saline-blood mixture. The injected ozone may be pure ozone or a mixture of ozone and pure oxygen. The ozonated blood is then intravenously reinfused back into the patient, typically at a rate of approximately 80 mL/hour.

In the event the patient suffers from addiction to benzodiazepines or alcohol (Box 86), the standard protocol is modified to include delivery of 100 mg phenytoin, trade name Dilantin, three times per day for five or six days.

In the event the patient suffers from significant detoxification effects (Box 88), the standard protocol is modified to include hyperthermia therapy on Days 2, 3, 4 and 5. Hyperthermia therapy includes 30 minutes per day in an infrared sauna or other means for exposing the patent to increased temperature.

In the event the patient suffers from restless syndrome (Box 90), the standard protocol is modified to replace the daily intravenous delivery of glutathione with daily intravenous delivery of 250 mg alpha lipoic acid (ALA). ALA is typically diluted into a 250 mL saline bag and provided to the patient intravenously over a 30 minute period for three to nine consecutive days. When either the patient's restless leg syndrome alleviates or the nine day period has expired, whichever occurs first, the daily delivery of ALA ceases and the standard protocol delivery of glutathione resumes.

In the event a patient suffers from low testosterone (Box 92), the standard protocol is modified to include testosterone replacement therapy. Normal levels of testosterone for men range from approximately 280-1,100 nanograms/deciliter (ng/dL), depending on age and health. Patient suffering from opioid addiction may have testosterone levels in the 100-200 ng/dL range. Testosterone replacement therapy may include providing a testosterone replacement pellet to the patient or other means for testosterone replacement known in the art.

Day 2

The beginning of the Restoration Program begins with NAD Amino Acids Addiction Therapy (see Box 100) including an intravenous NAD amino acids addiction protocol that, in some embodiments, includes nine to nineteen (9 to 19) consecutive days of treatment, depending on the addictive substance being treated. Patients suffering from polypharmacy, that is, addiction to multiple substances, typically require longer treatment durations than patients addicted to a single substance.

The patient is provided with a first liquid composition including NAD amino acid formulas based on the Dr. William Hitts Addiction Protocol. These formulas designed by colors corresponding to the NAD content of the formula: Red Formula (1200 mg NAD), Orange Formula (1100 mg NAD), Yellow Formula (1000 mg NAD), and Blue Formula (900 mg NAD). Each formula further comprises an amino acid mixture including L-threonine 2 mg, Glycine 2 mg, L-phenylalanine 2 mg, DL-phenylalanine 4 mg, and alanyl-glutamine dipeptide 4 mg, together with the aforementioned amount of NAD.

NAD formulas are preferably delivered over a period of 8 to 12 hours, and more typically about 10 hours, at a drip rate of 5-22 drops per minute. Different formulas are used in treatment of different addictive substances as follows (see Box 110):

| NAD+ Amino Acid Formula | Addictive Substance |
| --- | --- |
| Red | Benzodiazepines, Ambien, Lunesta, Sonata, Antidepressant (except Bupropion and Mirtazapine), Antipsychotics, Antiepileptics, GHB, and Barbiturates |
| Orange | Alcohol, Opiates, Suboxone, Heroin, and Methadone |
| Yellow | Nicotine, tobacco, marijuana, and cannabis |
| Blue | Cocaine, Crack, Methamphetamine, ADHD drugs, Methylphenidate, Adderall, Bupropion, Mirtazapine, LSD, Ecstasy, MDMA, Ketamine, PCP, pornography, sex, and gambling |

In some embodiments, one unit of NAD formula is provided per day during treatment. In other embodiments, 1.5 units of NAD formula are provided for three or four days of the first five days of NAD treatment (i.e., Days 2 through 6).

Day 2 of the program includes providing the patient with the appropriate NAD+ amino acid substance specific formula based on the patient's addictive substance being treated, delivered intravenously between 5-22 drops per minute. Day 2 further includes intravenous delivery of a second liquid composition including Myers nutritional cocktail (a solution including magnesium, calcium, B-vitamins and vitamin C) and intravenous glutathione (preferably 500 mg-1000 mg). 38 mL of Myers cocktail is diluted into a 250 mL saline bag and provided to the patient intravenously over a period of not less than 30 minutes and not more than 1 hour. The glutathione may be diluted into the same saline bag as the Myers cocktail.

Day 3

NAD Amino Acids Addiction Therapy continues with intravenous Myers nutritional cocktail, intravenous glutathione (preferably 500 mg-1000 mg), and intravenous NAD amino acid substance specific formula (15-22 drops/minute), as in Day 2. Quantities, methods and rates of delivery remain constant between days unless specified otherwise.

Day 4

NAD Amino Acids Addiction Therapy continues with intravenous Myers nutritional cocktail, intravenous glutathione (preferably 500 mg-1000 mg), and intravenous NAD amino acid substance specific formula (15-22 drops/minute), as in Day 7. The patient may take sublingual oral supplements of Niacin 15 mg and NAD 15 mg, one dose in the morning and one at night. In certain embodiments, the treating physician may recommend the patient take oral supplements and provide guidelines to the patient, whereby the patient selects and takes oral supplements at his or her own discretion.

Day 5 to the Penultimate Day (Day 9 Through 19)

Daily treatment continues with NAD Amino Acids Addiction Therapy, an intravenous Myers nutritional cocktail, intravenous glutathione (preferably 500 mg-1000 mg), and intravenous NAD amino acid substance specific formula (15-22 drops/minute), as in Day 2, and continuing the oral supplement regimen, as in Day 4. The duration of the treatment (ten to twenty days in total) is dependent upon the patient's response to the treatment and severity of the initial condition.

Final Day

NAD Amino Acids Addiction Therapy continues with an intravenous Myers nutritional cocktail, intravenous glutathione (preferably 500 mg-1000 mg), intravenous NAD amino acid substance specific formula (15-22 drops/minute), as in Day 2, and continuing oral supplement regimen, as in Day 4. The Final Day program further includes a follow-up medical psychiatric evaluation/consultation (see Boxes 120 and 130).

Figure 2A:
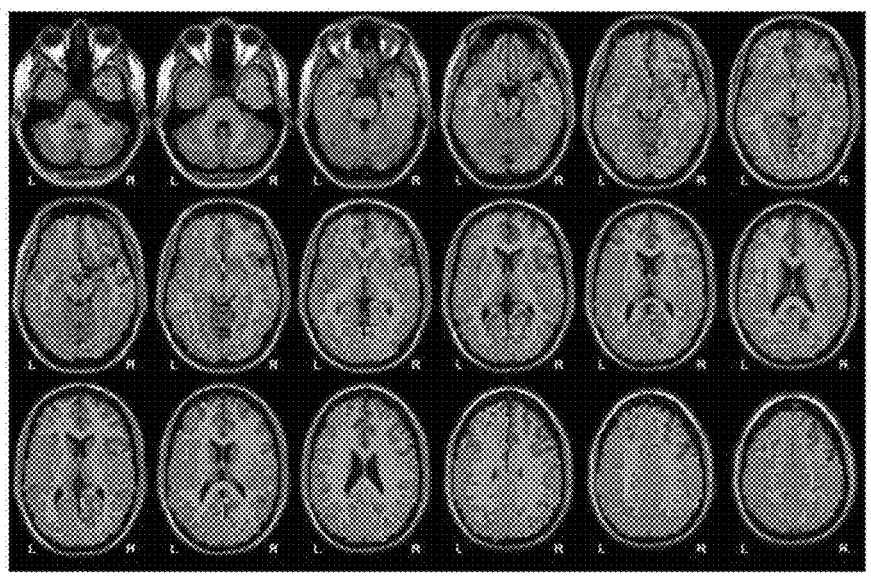
FIG. 2A depicts a series of standardized Low Resolution Brain Electromagnetic Tomography (sLORETA) scans at 25 Hz reconstruction of a patient's brain.
Figure 2A:
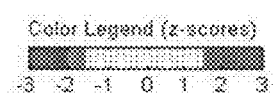
Figure 2B:
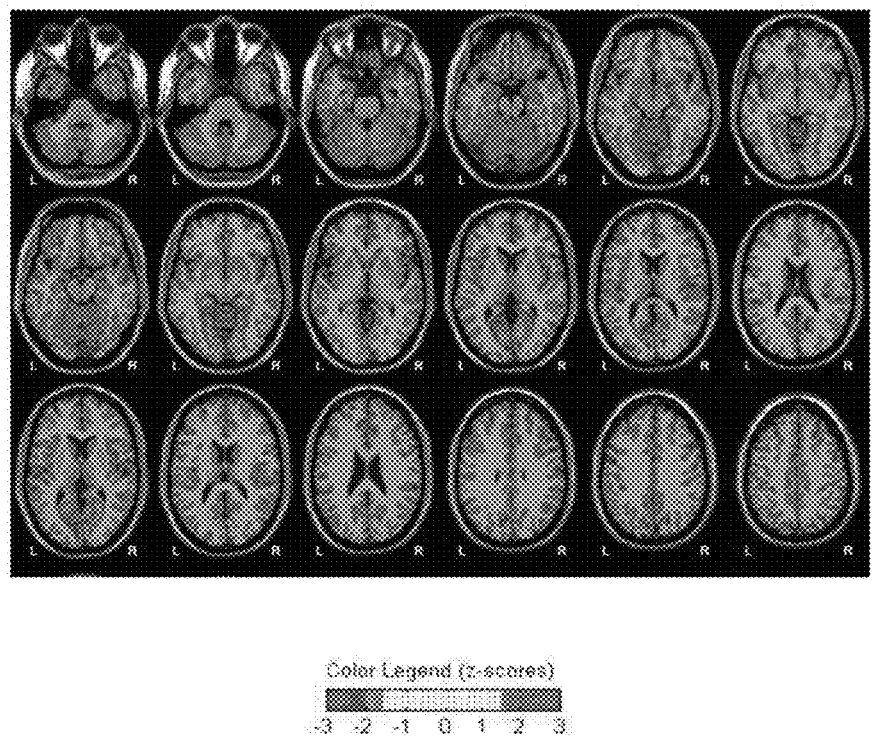
FIG. 2B depicts a series of sLORETA scans at 25 Hz reconstruction of the same patient's brain as in FIG. 2A. The scans in FIG. 2B were taken 13 days after the scans in FIG. 2A, the patient having undergone the treatment process of the present invention in the intervening period.

Referring now to FIGS. 2A and 2B, the figures display sLORETA scan of a patient's brain taken before (FIG. 2A) and after (FIG. 2B) having undergone the aforementioned treatment. The patient was a female, age 29, suffering from alcoholism. Multiple brain sections exhibiting a z-score of 3 in FIG. 2A indicate hyperactive and overactive portions of the brain. The patient reported feeling sick if she did not drink alcohol each morning, and suffered cravings and anxiety due to wanting to drink simply not to feel sick. After having undergone the treatment, as shown in FIG. 2B, no sections of the brain exhibit a z-score of 3. The patient reported feeling much more at ease after the treatment, and no longer felt sick if she did not drink alcohol in the morning. These results evidence the positive benefits on addiction recovery and general wellness provided by the disclosed treatment program.

The foregoing detailed description is given primarily for clearness of understanding and no unnecessary limitations are to be understood therefrom, for modifications can be made by those skilled in the art upon reading this disclosure and may be made without departing from the spirit of the invention.

The invention claimed is:

1. A method comprising:
    delivering a first liquid composition to a patient intravenously, the first liquid composition including NAD, threonine, glycine, phenylalanine, and alanylglutamine dipeptide;
    delivering a second liquid composition to the patient intravenously, the second liquid composition including a plurality of vitamins and a plurality of minerals; and
    delivering ozone to the patient intravenously.

2. The method of claim 1, further comprising delivering the first liquid composition at least once per day for at least two days.

3. The method of claim 2, wherein the first liquid composition is delivered to the patient intravenously between 8 hours and 12 hours per day.

4. The method of claim 1, further comprising delivering the first liquid composition at least once per day for at least nine days.

5. The method of claim 1, further comprising delivering the first liquid composition at least once per day for nine to nineteen days.

6. The method of claim 1, wherein the first liquid composition includes at least about 900 mg NAD.

7. The method of claim 1, wherein the first liquid composition includes a mixture of D-phenylalanine and L-phenylalanine.

8. The method of claim 1, wherein the second liquid composition includes B-vitamins, vitamin C, magnesium, and calcium.

9. The method of claim 1, wherein the second liquid composition further includes one of glutathione and alpha lipoic acid.

10. The method of claim 9, wherein the second liquid composition includes between 500 mg and 1,000 mg glutathione.

11. The method of claim 1, further comprising delivering the second liquid composition at least once per day for at least two days.

12. The method of claim 11, wherein the second liquid composition is delivered to the patient intravenously between 30 minutes and 1 hour per day.

13. The method of claim 1, further comprising delivering the second liquid composition at least once per day for at least nine days.

14. The method of claim 1, further comprising delivering the second liquid composition at least once per day for nine to nineteen days.

15. The method of claim 1, wherein delivering ozone to the patient intravenously comprises drawing blood from the patient, infusing the blood with ozone, and intravenously delivering the blood back to the patient.

16. The method of claim 1, further comprising drawing blood from the patient, exposing the blood to UV light, and intravenously delivering the blood back to the patient.

17. The method of claim 1, further comprising providing to the patient at least one of acupuncture treatment, chiropractic adjustment, testosterone replacement therapy, massages, application of pain cream, UV light therapy, and oral supplements of niacin and NAD.

18. A method comprising:
    delivering a first liquid composition to a patient intravenously, the first liquid composition including NAD, threonine, glycine, phenylalanine, and alanylglutamine dipeptide; and
    delivering ozone to the patient intravenously.

19. A method comprising:
    delivering a first liquid composition to a patient intravenously, the first liquid composition including nicotinamide adenine dinucleotide, threonine, glycine, phenylalanine, and alanylglutamine dipeptide;
    delivering a second liquid composition to the patient intravenously, the second liquid composition including a plurality of vitamins, and a plurality of minerals; and
    drawing blood from the patient, exposing the blood to UV light, and intravenously delivering the blood back to the patient.

20. The method of claim 19, wherein the second liquid composition further includes one of glutathione and alpha lipoic acid.

21. A method comprising:
    delivering a first liquid composition to a patient intravenously, the first liquid composition including NAD, threonine, glycine, phenylalanine, and alanylglutamine dipeptide; and
    drawing blood from the patient, exposing the blood to UV light, and intravenously delivering the blood back to the patient.

* * * * *